United States Patent [19]
Shaposka et al.

[11] Patent Number: 5,248,359
[45] Date of Patent: Sep. 28, 1993

[54] STERILE ENTRY/EXIT TOTAL CONTAINMENT PROCESS FOR CLOSED SYSTEMS USING PLASTIC TUBES

[75] Inventors: John B. Shaposka; Dudley W. Spencer, both of Wilmington, Del.

[73] Assignee: Denco Inc., Wilmington, Del.

[21] Appl. No.: 888,013

[22] Filed: May 26, 1992

Related U.S. Application Data

[62] Division of Ser. No. 569,855, Aug. 20, 1990, Pat. No. 5,141,592.

[51] Int. Cl.⁵ ............................................. B32B 31/26
[52] U.S. Cl. .................................. 156/158; 156/304.2; 156/304.5; 156/304.6
[58] Field of Search .................. 156/158, 304.2, 304.5, 156/304.6, 518, 530, 515, 251

[56] References Cited

U.S. PATENT DOCUMENTS

| | | | |
|---|---|---|---|
| 4,369,779 | 1/1983 | Spencer | 156/304.2 |
| 4,507,119 | 3/1985 | Spencer | 156/304.2 |
| 4,516,971 | 5/1985 | Spencer | 156/304.2 |
| 4,737,214 | 4/1988 | Leurink et al. | 156/304.2 |
| 4,793,880 | 12/1988 | Shaposka et al. | 156/304.2 |
| 4,913,756 | 4/1990 | Shaposka et al. | 156/158 |
| 4,933,036 | 6/1990 | Shaposka et al. | 156/158 |

*Primary Examiner*—Caleb Weston
*Attorney, Agent, or Firm*—Connolly & Hutz

[57] ABSTRACT

A process for sterile entry/exit into a closed system permits safe addition of reagent/nutrient/process modules, etc., removal of biological samples or depleted process modules such as filters, etc. all without exposing the operator to possibly dangerous materials such as blood and without endangering the contents of the system such as in cell-culturing. A novel welder and process is disclosed to illustrate the process.

17 Claims, 7 Drawing Sheets

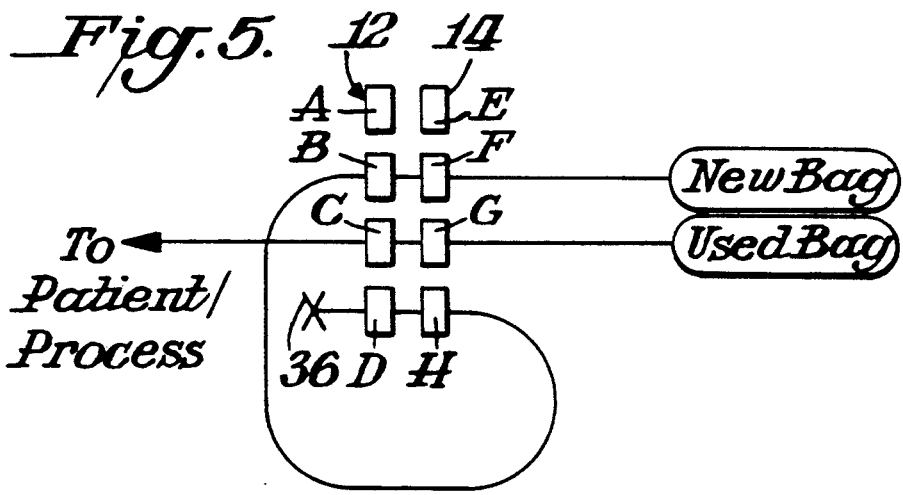
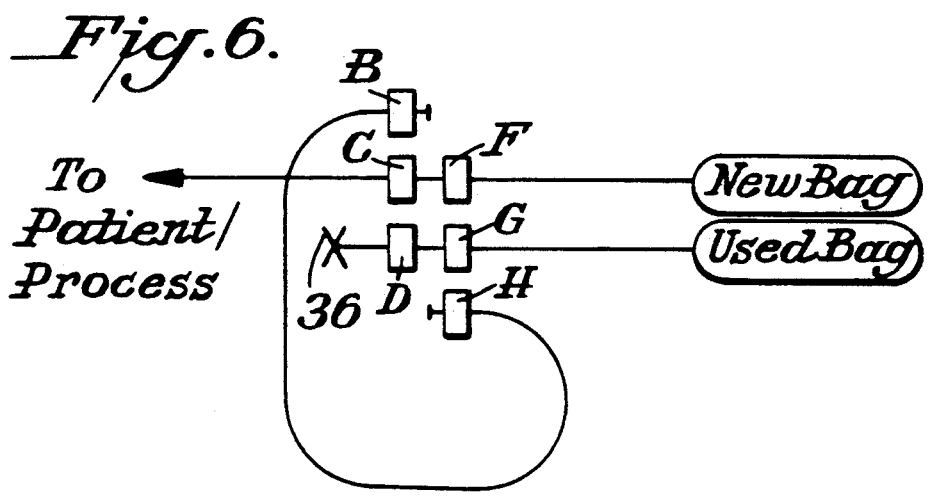
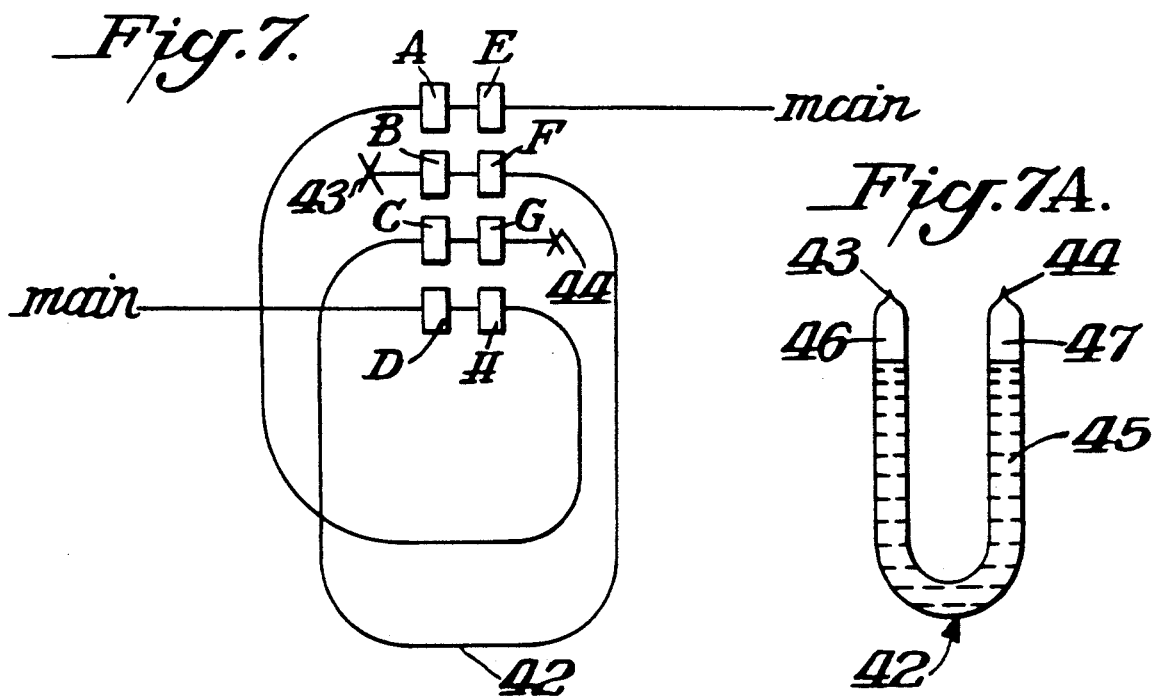

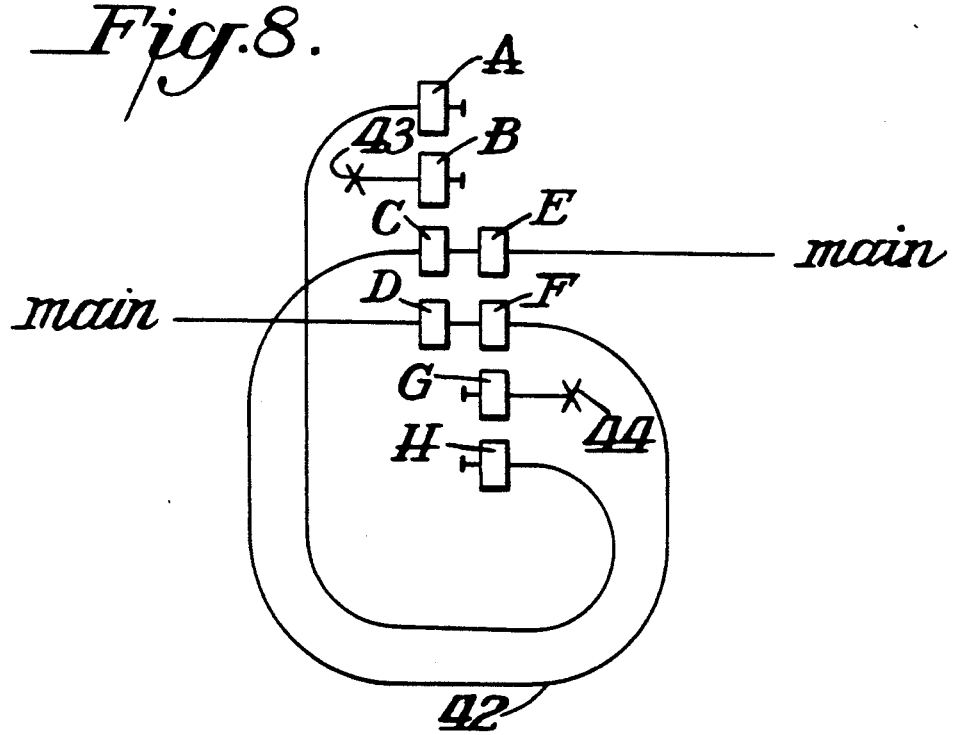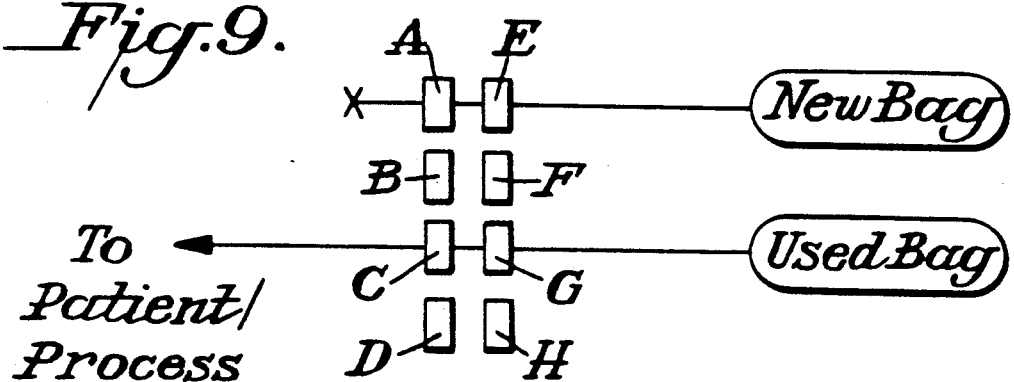

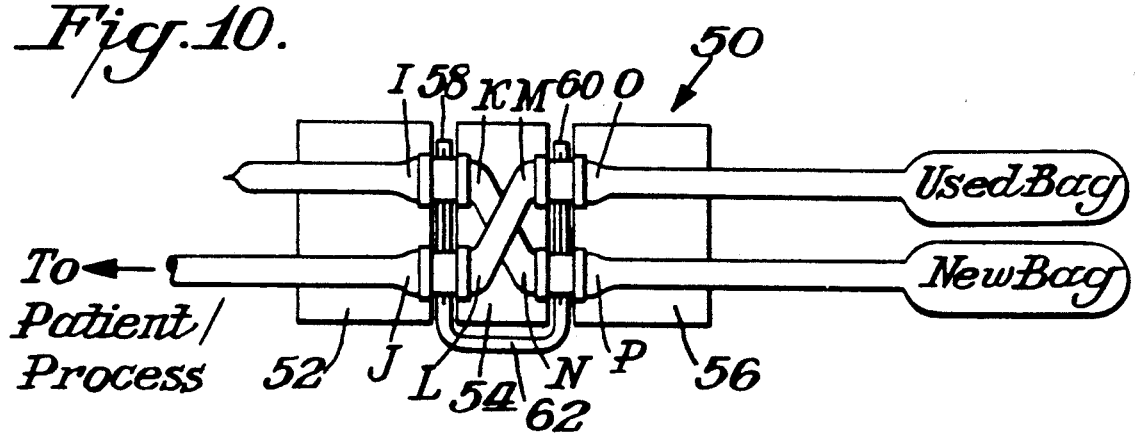
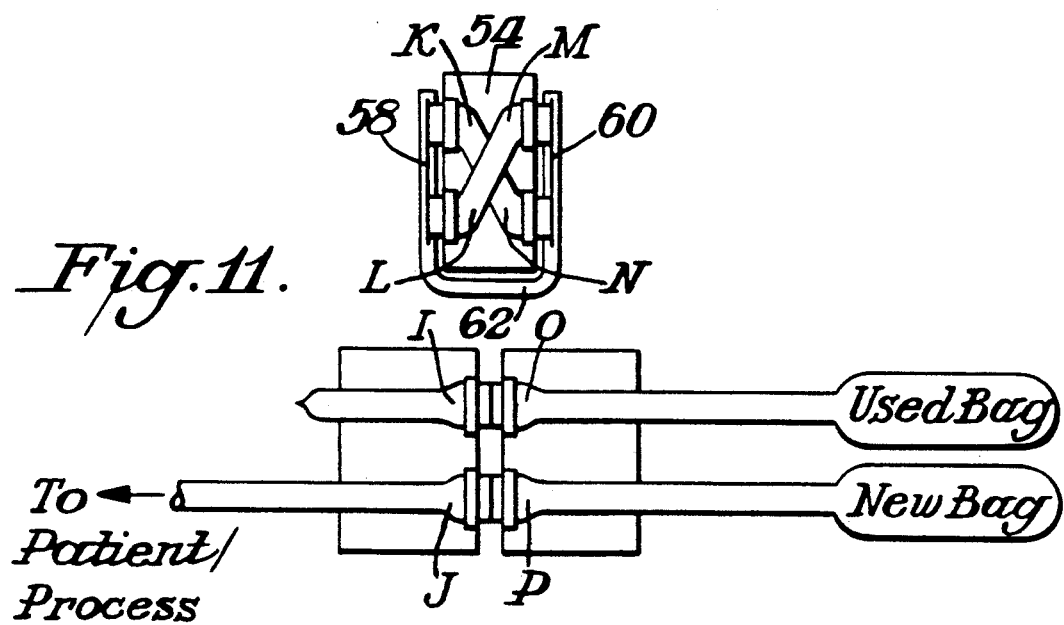
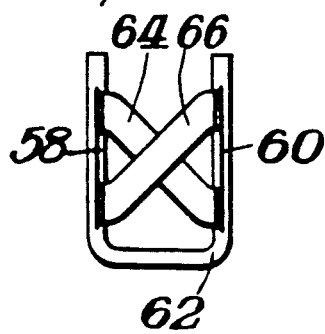

Fig. 17.
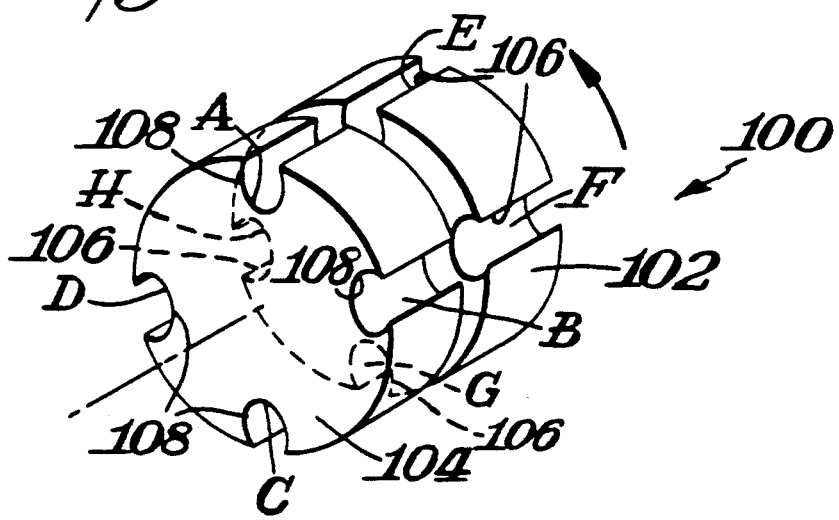
Fig. 18.
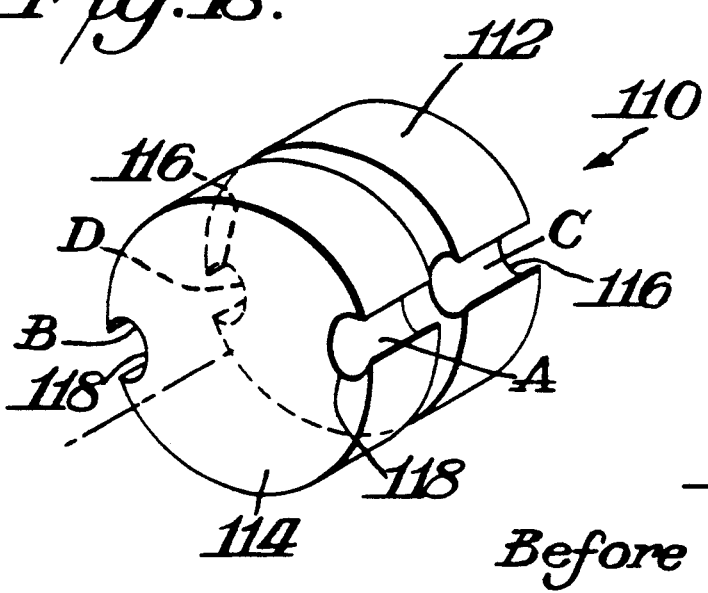
Fig. 19.

STERILE ENTRY/EXIT TOTAL CONTAINMENT PROCESS FOR CLOSED SYSTEMS USING PLASTIC TUBES

CROSS-REFERENCE TO RELATED APPLICATION

This application is a divisional of application Ser. No. 07/569,855 filed Aug. 20, 1990, U.S. Pat. No. 5,141,592.

BACKGROUND OF INVENTION

Various techniques exist for the sterile welding of plastic tubes. Particularly noteworthy techniques are described in U.S. Pat. No. 4,793,880 of which I am a co-patentee. Other patents disclosing welding or sealing techniques for plastic tubes include U.S. Pat. Nos. 4,753,697; 4,770,735; 4,832,773; 4,864,101; 4,897,138; 4,913,756 and 4,933,036. In each of these patents I am a co-patentee with Dudley W. C. Spencer. Further patents of Dudley W. C. Spencer which are pertinent are 4,369,779; 4,412,835; 4,507,119; 4,516,971; 4,610,670 and 4,619,642.

While the above patents disclose variations of techniques for the sterile welding or sealing of plastic tubes, they focus primarily on the welding or sealing processes. With the advent of AIDS, the safe handling of dangerous biological fluids and safeguarding the nation's blood supply has assumed major significance. It would be desirable for example, for blood processing centers to be able to handle blood separations without the risk of exposure to the technician, CAPD patients need to be able to safely bag-off and bag-on, to automatically seal the discarded bag, or to be able to take a sample during bag-off for lab analysis. Hospital personnel need a way to avoid Hepatitis when changing urinary drainage bags. Farmers could inject a known quantity of reagent such as an insecticide into a closed system without fear of exposure from concentrates. Monitoring samples need to be safely taken from bioreactors and needed reagents or nutrients injected without fear of contamination. Filter, and other types of process modules need to be sterilely installed or removed.

Except for U.S. Pat. No. 4,753,697 the prior art does not address the problem of total containment of the tube contents. Even that patent is silent on anything other than welding one stub end to the other to effectively seal off the stubs. None of the other existing technologies can address all of these needs without an awkward double or triple welding step. Since they require a multi-step procedure, there exists a very high risk of mistakenly welding the wrong tubes together During all the handling, the lightly tack-sealed stub-ends run a very large risk of leaking, contaminating both the operator and the system.

SUMMARY OF INVENTION

An object of this invention is to provide a device and processes capable of:

Removing a sample from a closed system in one step without compromising the sample, system or operator.

Inserting a sample or process module into a closed system in one step without compromising either the sample, the system or the operator.

Removing a sample or process module and inserting a new process module in one step without compromising the old sample, the new sample, the system or the operator.

Safely segmenting a system into two parts in one step without compromising the system or the operator.

Exchanging a new supply container for a depleted one while simultaneously producing a safe sample ring for assay.

Producing a "sample ring" with tube ends welded together for safety.

Safely removing a depleted process module such as a filter in such a way that the module tube's distal ends are fused so as to totally contain the tube/module contents.

Permit the safe handling of process fluids; without the need for syringe needles, thereby minimizing the hazards of biological waste disposal and accidental puncture.

A further object of this invention is to provide a device capable of performing the above weld/seal processes.

In accordance with one embodiment of this invention the device includes a pair of side by side tube holders or clamp assemblies, each of which is capable of holding four tube sections. The tube holders are mounted whereby one of the holders may be moved longitudinally to effect a realignment of the tube sections and whereby one of the holders may be moved laterally to press certain of the cut tube sections into contact with each other. A heated wafer is provided for moving up and down into the space between the tube holders to cut the tube sections and heat them so that the realigned tube sections may be welded together The invention may be practiced to insert a tube section into a line and/or to remove a tube section in ring form welded to itself. By inserting a tube section a reagent may be introduced. Similarly insertion of a tube section permits the introduction of a physical member into the line such as a filter, a barrier, a coating, a membrane or a coagulant. The ability to remove the ring form tube section permits the taking of sample which is totally contained thereby maximizing safety in the handling of the sample.

In a further embodiment of this invention three side by side tube holders are provided, each of which is capable of having two tube sections mounted thereto. The central tube holder has its tube sections crossing each other so that a realignment is effected without having to longitudinally move either end tube holder by simply removing the central holder after the tube sections have been cut and then moving one of the end tube holders toward the other end holder

THE DRAWINGS

FIGS. 4-7 are plan views schematically showing variations in the operation of the device in FIGS. 1-3;

FIG. 7A is a plan view of a tube section used in the operation illustrated in FIG. 7;

FIGS. 8-9 are plan views schematically illustrating further variations in the operation of the device of FIGS. 1-3;

FIG. 10 is a top plan view of a modified form of device in accordance with this invention;

FIG. 11 is a top plan view of the device of FIG. 10 in a later phase of operation;

FIG. 12 is a top plan view schematically showing a wafer and tube section unit resulting from the device of FIGS. 10-11.

FIG. 17 schematically shows in perspective an alternative device in accordance with this invention;

FIG. 18 shows a modified form of the device of FIG. 17; and

FIG. 19 schematically shows a pair of tubes before and after use of the devices of FIGS. 17-18.

DETAILED DESCRIPTION

The welding aspects of the present invention is based upon the techniques generally described in the above noted patents and in particular U.S. Pat. No. 4,793,880 the details of which are incorporated herein. Accordingly, a description of all of those details is not necessary except where it will facilitate an understanding of the variations which form features of this invention.

Figure 1:
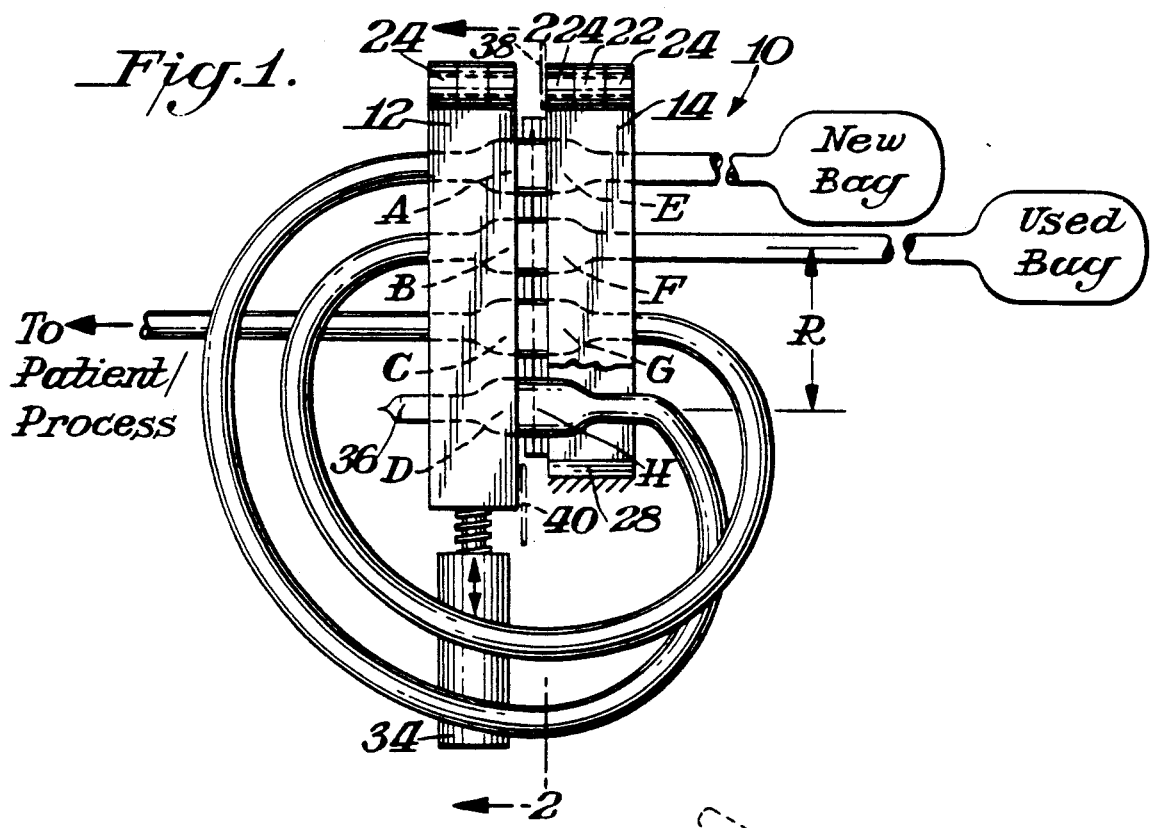
FIG. 1 is a top plan view illustrating a device for the sterile welding or sealing of plastic tubes in accordance with this invention.
Figure 2:
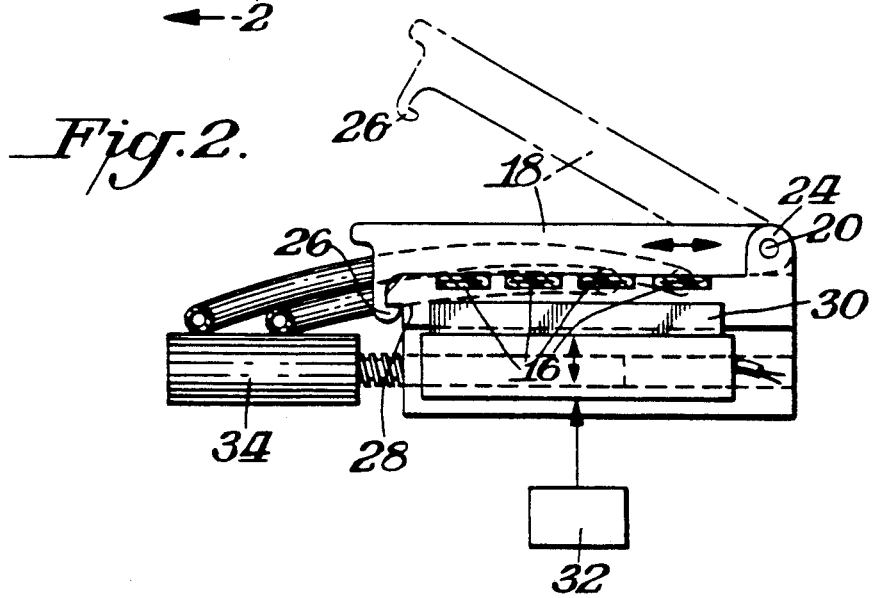
FIG. 2 is a cross-sectional view in elevation taken through FIG. 1 along the line 2—2.

FIGS. 1-2 illustrate a device 10 which comprises a welder capable of offering all of the advantages of the welder described in U.S. Pat. No. 4,793,880 in addition to further valuable features unique to this invention. As shown therein device 10 includes a pair of side by side clamp assemblies or holders 12,14. Each holder is provided with a set of at least two or three but preferably four grooves 16 for receiving four plastic tube sections. Each holder further includes a clamp mechanism 18 hingedly mounted around axle 20 for flattening the tube sections clamped therein. Any suitable hinge means may be used, such as a tongue 22 on clamp member 18 extending between a pair of upstanding ears 24 on each respective holder 12,14. Clamp 18 is locked in position in any suitable manner such as by a hook portion 26 which is engaged under projection or lip 28 of each respective holder as shown in solid lines in FIG. 2. When clamp 18 is thus in the clamped position shown in solid lines each tube is clamped to a flattened condition.

In the practice of this invention, the tubes may be fluid filled and flattened or dry and not flattened. 12,14 is indicated by the letters A through H to facilitate a description of the operation of device 10.

In accordance with this invention, a heated wafer 30 is provided mounted in any suitable manner for moving up and down in the Z direction into and out of the space between the two arms or holders 12,14 perpendicular to the plane of the clamped tube sections. In the illustrated embodiment, for example, wafer 30 is mounted on a reciprocating device 32. The direction of movement of wafer 30 and the arrangement of the tubes represent a significant advantage over other arrangements such as in U.S. Pat. No.; 4,793,880 in that the "fin effect" seen in other wafer arrangements is greatly minimized and all tubes see a much more uniform heat profile. Also, the arrangement makes possible the use of a special tube pocket parallel to but displaced from the plane of the rest of the tube pockets by approx ½ of one tube wall thickness as taught in U.S. Pat. No. 4,913,756. An additional difference from that patent is that each holder or arm is capable of holding four tube sections whereas each holder in the device illustrated in the patent holds only two tube sections.

As illustrated arm or holder 12 is mounted to a drive device 34 for longitudinally moving holder 12 in the Y direction with respect to holder 14. Accordingly, holder 12 may be considered a movable clamp assembly while holder 14 may be considered a stationary clamp assembly. Additionally, one of the clamp assemblies, such as holder 12, is laterally movable in the X direction as well as being longitudinally movable in the Y direction so that after the tube sections have been realigned upon movement of holder 12 in the Y direction, the tube sections may be pressed into contact with each other by movement of holder 12 in the X direction. It is to be understood, of course, that the invention may be practiced with either of the holders movable in the X direction and/or the Y direction.

Figure 3:
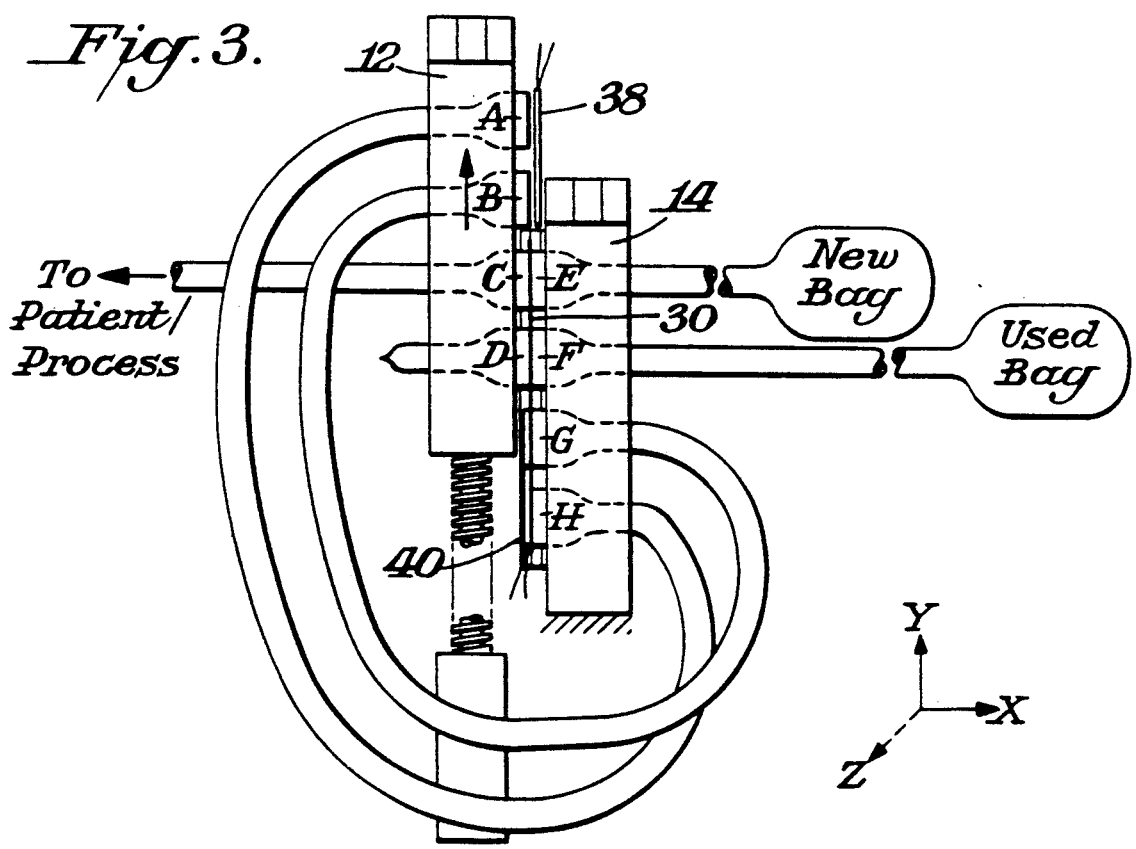
FIG. 3 is a top plan view of the device of FIGS. 1-2 after the tubes have been realigned.

FIGS. 1 and 3 illustrate one manner of using device 10, wherein a patient on CAPD must sterilely exchange a used bag of dyalysate for a new bag. FIG. 1 shows the placement of the tubes in device 10 before the severing and welding operations. As shown therein the new bag would have its tube placed in the appropriate endmost groove of holder 14 and across the aligned groove of holder 12 as indicated by the letters E, A. The same tube would then be placed over the opposite endmost grooves 16 in holders 14 and 12 as indicated by the letters H,D with the factory formed stub end 36 being sealed. The used bag would have its tube span intermediate grooves 16 of holders 14 and 12 as indicated by the letters F and B and then would again span holders 14 and 12 as indicated by the letters G and C. That tube would ultimately lead to the patient.

In operation, after the tubes have been placed in device 10 in the manner illustrated in FIG. 1, the wafer 30 would be heated and then rise in the Z direction to severe all four sections. At this point, the movable clamp assembly or holder 12 moves in the Y direction by the distance R to realign the various severed tube sections as shown in FIG. 3. In this realigned position, the tube sections at locations C and E are aligned with each other as are tube sections at locations D and F. Wafer 30 would then be lowered away from the spacing between the tube holders 12,14. As shown in FIG. 3 a pair of radiant heaters 38,40 are also provided. Heater 38 is a stationary heater while heater 40 is attached to the clamp mechanism or holder 12 so that it moves with holder or movable clamp mechanism 12. Heater 38 functions to seal the tube ends at locations A,B, while heater 40 functions to seal the tube ends at locations G,H. The tube ends at locations C and E and at locations D and F are melted by wafer 30 so that the corresponding tube ends are welded together upon relative movement in the X direction of one of the holders with respect to the other holder. For example, in the embodiment illustrated in FIG. 3 holder 12 is both longitudinally movable in the Y direction and laterally movable in the X direction. As a result, when the tube ends at locations C and E are welded together the new bag is placed in communication with the tube leading to the patient. Similarly, when tube sections at locations D and F are welded together the used bag is sealed by being associated with stub end 36. This is a distinct and significant advantage of the invention.

In operation, after the tube ends have been cut and holder 12 has been moved longitudinally. The system pauses with the tube sections still on wafer 30 to build up a melt pool. The optional stationary and moving heaters 38,40 start to begin the sealing of the stub ends at locations A, B, G and H. The wafer 30 then drops out of the way below the plane of the cut tubes (as shown in FIG. 2) and the movable clamp assembly 12 moves laterally in the X direction toward stationary clamp assembly 14 to effect the weld. Thus, while the weld is cooling the stub ends A, B, G and H are sealing.

At the end of the stub sealing cycle the clamps 18 are opened and the stubs at locations A, B, G and H can be discarded. Because during the clamping operation the stubs are partially flattened, they will tend to be at a partial vacuum so that the hazards of tube handling are minimal.

Moreover, because the tubes are flattened as shown in FIG. 2 the amount of wafer sticking out of the heater assembly is very small so that there will exist a very favorable temperature gradient across the wafer in the Z direction. The wafer 30 will be easy to keep at a uniform temperature because the "fin effect" is minimized.

The tubes are very easy to load with the invention in that no significant bending of the tubes is required. Thus device 10 lends itself to automatic tube loading accordingly making possible high volume work. Device 10 can also use a wafer 30 which is simple, small and inexpensive. The use of device 10 makes possible the ability to automatically inject used wafers and to feed new wafers. If desired, device 10 could incorporate wrapping pins to make tube installation fool proof. With device 10 it is possible to seal tubes in the same device without any changes whatsoever to the mechanism or process. The only handling required is done in the tube loading.

Figure 4:
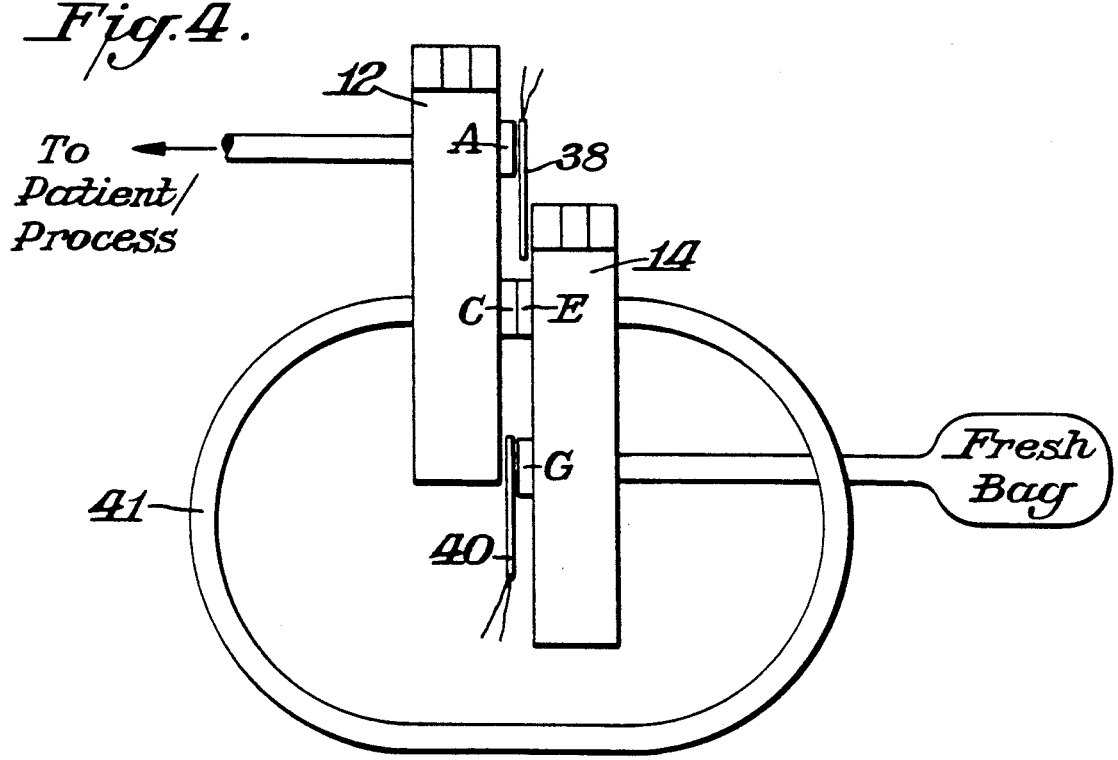

FIG. 4 illustrates a variation which is capable of simultaneously "bagging off" a patient and obtaining a sample ring. FIG. 4 illustrates the arrangement of the tube sections after the welding operation. Initially, the fresh bag with its tube end location G would extend across holder 14 and then would extend across holder 12 at location C. The tube would again extend across holder 14 at location E and across holder 12 at location A with the tube then going to the patient. When it is desired to obtain a sample ring, the tube sections would be cut and melted and then shifted to the position illustrated in FIG. 4. As a result, a closed loop 41 would form which is welded at locations C and E. The end at location A leading from the patient would be sealed by heater 38 while the end at location G leading from the fresh bag would be sealed by heater 40. The resultant sample ring 41 could be used for various purposes such as bio-tech testing. If desired the fresh bag tube could later be welded to the patient tube.

FIGS. 5-6 illustrate a manner of using device 10 so as to result in the capping of the used dyalysate bag or CAPD with a slightly modified cycle. As shown therein, the new bag would extend across holders 12 and 14 as indicated by locations F and B. The tube would then loop around and again extend across the holders as indicated by locations H and D and have a factory sealed stub end 36. The used bag would extend across the holders at locations G and C and lead to the patient After the tubes sections are cut and realigned the tube sections are in the position shown in FIG. 6. The tube ends at locations B and H would be sealed while the tube sections at locations C and F and at locations D and G would be welded together The result is that the new bag is welded to the tube section leading to the patient while the used bag is welded to stub end 36. The tube section between locations B and H could be discarded. As is apparent, the locations A and E in holders 12 and 14 are not used in this practice of the invention.

In this embodiment, since the stub 36 comes from the new bag, it is safe and sterile. Accordingly, it is not necessary to use the radiant heaters to seal the ends.

FIGS. 7-8 show yet another practice of this invention in a variation of the operation of device 10. In this variation the basic cycle can be used to splice in a segment of tube 42 into an existing line. This might be done, for example, to add a known amount of reagents into a closed system or to make a section of tubing longer as in CAPD. FIG. 7 illustrates the loading of the tubes so that the main tube extends across locations E and A and then across locations H and D. The sealed tube section 42 would extend across locations B and F and then across locations C and G with the sealed ends being indicated by the reference numerals 43,44 so that a known quantity of reagent is injected. The tube section 42 would, for example, contain a reagent shaken down to keep the reagent away from the sealed ends 43,44. FIG. 7A for example shows the tube section 42 wherein the reagent is indicated by the reference numeral 45 and the reagent free end areas is indicated by the reference numerals 46,47.

After the tube sections are cut and realigned, the tube sections are located as shown in FIG. 8. As indicated therein a continuous tube is formed by having the tube section 42 spliced thereto. This continuous tube section extends across locations E and C and then across locations F and D. The discardable section would extend between locations A and H and the discardable stubs 43 and 44 would be at locations B and G. If in the practice of the invention shown in FIGS. 7-8 there were a misloading of the pre-sealed section 42, all that would happen would be a rejoining of the main tube with the obtaining of a ring sample.

It should be appreciated that the device 10 is of course capable of achieving the same type of linear welds as described in U.S. Pat. No. 4,793,880. In this respect, as shown in FIG. 9, locations B, D, F and H would not be used and the tube from a new bag would be placed across locations E and A while the tube from a used bag would be placed across locations C and G. After cutting, the realignment would result in location C being placed opposite location E so that the new bag tube would be welded to the tube leading to the patient. With this arrangement it is possible to simultaneously weld more than one tube.

FIGS. 10-12 illustrate further variations of this invention which depart from the practices in the above described patents. As shown in FIGS. 10-11 device 50 includes three side by side holders or clamp mechanisms 52,54,56. These clamp mechanisms make the welding of tube sections possible without requiring the same type of longitudinal realigning step as previously described. Holders 52 and 56 are the end holders which would be constructed similarly to previously described holders 12,14 except that longitudinal movement is not necessary. These holders would include locations I and J in end clamp mechanism 52 and locations O and P in end clamp mechanism 56. Locations K, L, M, and N are in central clamp mechanism 54. A space would be provided between the adjacent pairs of clamp mechanisms 52,54 as well as 54,56. These spaces would accommodate a heated wafer 62 having cutting edges 58,60 located, for example, in the gaps below the plane of the tubes as previously described.

FIG. 10 illustrates a loading operation wherein a used bag would be placed in clamp mechanism 56,54 across location O and M. The tube would then extend downwardly and across the gap between clamp mechanisms 54,52 at locations L and J. Similarly, a new bag would extend across the three clamp mechanisms at locations I, K, N and P. In operation, after the tubes are loaded in the clamp mechanisms, the wafer 62 and its edges 58,60 would be heated and would rise, for example, in the Z direction to sever all of the tubes at the four sets of locations. The wafer 62 would pause to allow a melt pool to build. The central clamp mechanism 54 would then move laterally and the wafers may move with it as shown in FIG. 11. The end clamp mechanisms 52,56 would then move toward each other by laterally moving one or both clamp mechanisms so that the welding occurs at locations I and 0 for the used bag and locations J and P for the new bag. Accordingly, the used bag would be sealed while the new bag would communicate with the patient. The stubs between locations K and N and between locations L and M on the central clamp location 54 could be discarded.

The central clamp could be designed as shown in FIG. 12, wherein the central clamp 54 has a U-shaped wafer 62 which extends along both sides thereof having cutting edges 58 and 60. In this manner, when the stub ends 64,66 are removed from central clamp mechanism 54, the U-shaped wafer 62 would remain secured to the stub ends so that the wafer and stub ends could be disposed of as a unit. FIG. 12 illustrates the disposable unit resulting from the stub ends and U-shaped wafer being removed from central clamp mechanism 54. In this respect, it is noted that PVC which is the conventional material used for such plastic tubes normally bonds very tenaciously to copper wafers. Accordingly, when the clamp mechanism is designed to at least partially flatten the stubs, the result is a partial vacuum in the stubs upon removal in the clamps. Consequently, the disposable unit will be very safe and secured when it is disposed. It is not only bonded to the surface, but also sticks to the surface like a suction cup.

If desired separate wafers could be mounted on each side of central holder 54, rather than a single U-shaped wafer 62.

Figure 13:
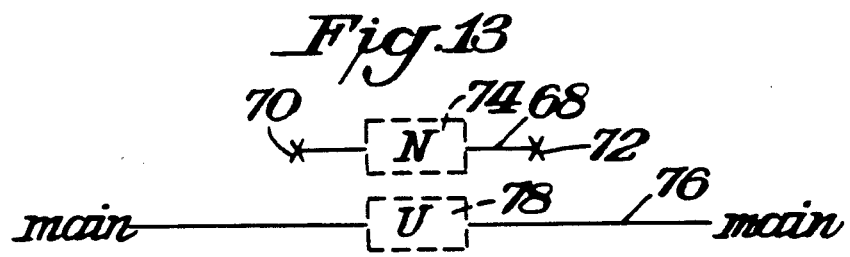
FIG. 13 schematically shows a tube section and a main line.

FIGS. 13-16 show a variation of the invention which is particularly usable for introducing a tube section or process module into a main tube line and for simultaneously obtaining a ring sample. FIG. 3, for example, illustrates a tube section 68 having a pair of factory sealed stub ends 70,72. The tube section also includes a portion 74 indicated by the dashed lines which need not be of tubular form, but could be of any suitable construction in accordance with the intended use for introducing that tube section as later described. For example, portion 74 could contain a known reagent in liquid, solid or powder form such as for introducing nutrients, inoculants (e.g. bacteria, yeast) pharmaceuticals (e.g. drugs) or other known reagents which could, for example, indicate by a change in color the presence of the AIDS virus. Similarly, portion 74 could contain a known type of physical member such as a filter (e.g. for separating plasma from the cells), a barrier, a coating, a membrane or a coagulant. FIG. 13 also illustrates a main tube 76 which would have a portion 78 comparable to the portion 74 of the tube section 68, except that portion 78 is the used portion or process module which is intended to be replaced.

Figure 14:
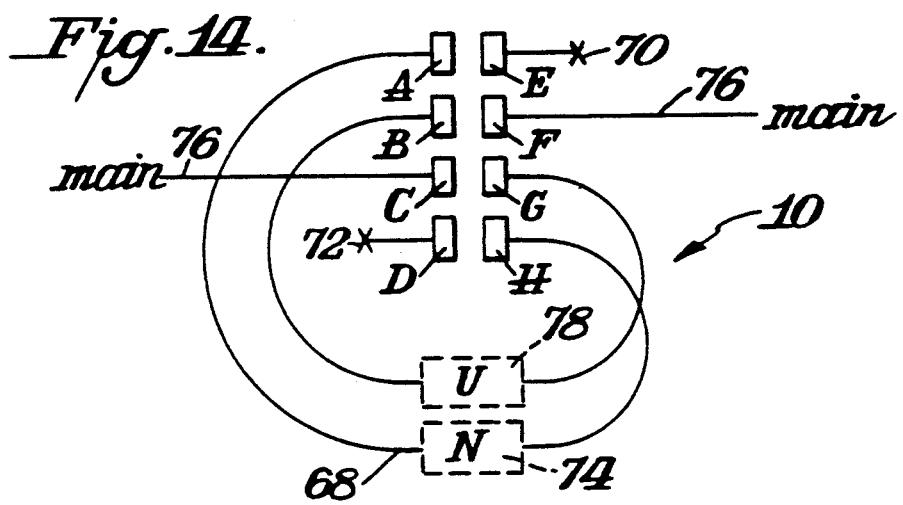
FIGS. 14-15 are plan views showing the tube section and main line of FIG. 13 before and after use of the device of this invention.
Figure 15:
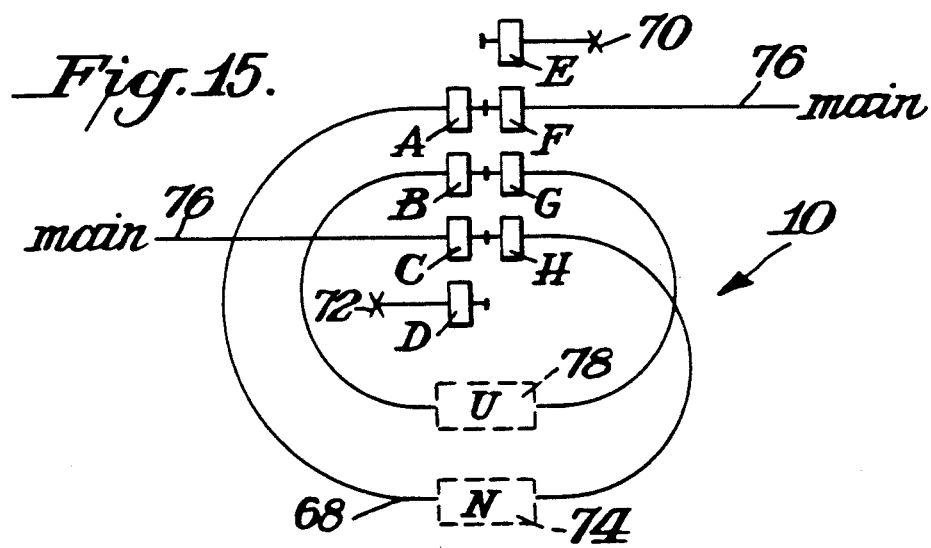
Figure 16:
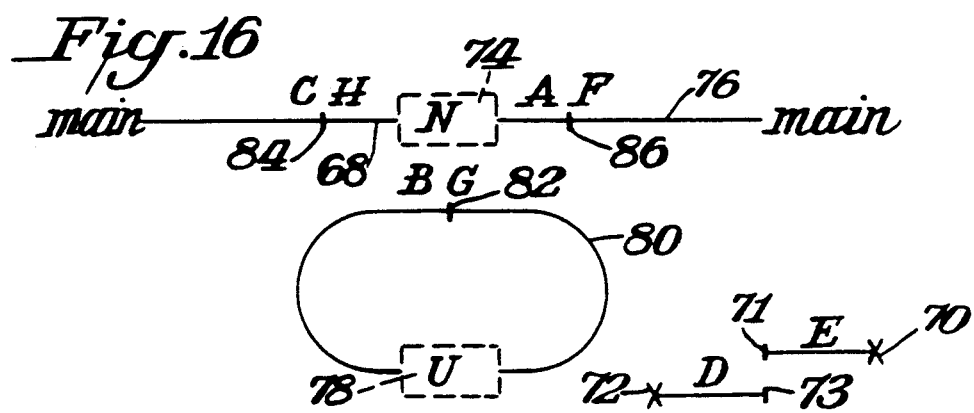
FIG. 16 shows the components resulting from the practice of FIG. 15.

FIG. 14 illustrates the device 10 in its condition wherein the tube section 68 or new process module and the main tube 76 are loaded in the respective holders. FIG. 15 illustrates device 10 after the cutting and realignment operation. FIG. 16 illustrates the various components resulting from the operation of FIG. 15 after those components have been removed from device 10. As shown in FIG. 16, four components result. These components comprise the main tube 76 which now includes the tube section 68 or new process module welded at locations 84,86 to thereby contain the new portion 74 to introduce the reagent or physical member a previously described. In addition, FIG. 16 illustrates a ring sample 80 being joined together at portion 82 and which includes the used portion or process module 78 which had previously been in main tube 76. Finally, a pair of end sections are also formed One end section includes the factory seal 70 and the closed portion 71 formed by the welding operation of FIG. 15. In addition, a further portion results having the factory sealed stub 72 and the opposite closed portion 73. It is to be noted that the end portion 71 and 73 need not be closed but could remain open since these loose ends will be discarded.

It should be appreciated that tube sections, such as tube section 68 of FIG. 13 or tube section 42 of FIG. 7A nee not be a completely flexible tube section. What is critical, however, where such tube section is to be inserted into a larger line is that at least a portion of the tube section is flexible to permit a bending to take place so that both ends of the tube section could be disposed parallel to each other when placed in the device. In the preferred practice of the invention both ends and preferably the major or entire portion of the tube section is flexible.

In the preferred practice of this invention, the device includes flat holders for clamp assemblies. FIG. 17, however, illustrates a variation where the pockets or grooves are formed in circular holders or disks. Specifically, FIG. 17 illustrates such a device 100 having a movable holders 102 which would rotate as indicated by the arrow to effect the realignment and which could move transversely towards its adjacent holder or clamp assembly 104. A set of four grooves or pockets 106 is formed in holder 102 for selective alignment with a corresponding set of four grooves or pockets 108. In practice device 10 would be loaded with the tubes placed in aligned pockets 106 and 108, similar to the linear version illustrated in FIG. 1. For example, the main tube could go through pockets F, B, G and C and the new module or tube section could go through E, A, H and D. A pivoting wafer (not shown) would rotate about the axis to sever all of the tubes and holder or clamp assembly 102 would rotate 90° to realign the tubes As a result, all tubes would mate so as to simultaneously produce four welds Although the wafer is preferably pivotally mounted, it may move transversely into and out of the gap between the holders.

FIG. 18 shows a simplified version wherein device 110 is of the two tube pocket welding structure. As indicated therein clamping assemblies 112 and 114 are provided which would be similar to clamp assemblies 102,104 of FIG. 17, except that each clamp assembly would have only two sets of grooves or pockets. Thus, FIG. 18 illustrates clamp assembly 112 to have a pair of pockets 116 which may be selectively aligned with the pair of pockets 118 in clamp assembly 114. After device 110 has been unloaded and the tubes cut, the movable clamp assembly 112 is rotated 180° so as to realign the cut tube ends.

FIG. 19 illustrates a pair of tubes which may be loaded, cut and then welded in either of the devices 100 of FIG. 17 or device 110 of FIG. 18. As shown in FIG. 19 one tube 120 would be placed in the grooves or pockets at the locations A and C of, for example, FIG. 18 while the other tube 122 would be placed in the grooves at locations B and D during the loading operation. After the tubes 120 and 122 have been cut, and clamp assembly 112 rotated 180° the result is illustrated in the lower portion of FIG. 19 wherein two joints 124 and 126 cause pairs of cut tube sections to be welded together.

A significant feature of this invention which opens up an entirely new field for the safe handling of toxics and contaminated materials is the ability to insert and/or remove tube sections from a main tube. In particular, the ability to simultaneously remove a sample or process module while installing a new module or reagent represents a significant feature of this invention that has heretofore not been possible.

As can be appreciated, this invention provides an effective manner of achieving a variety of different results These results include the ability to remove a sample ring, such as illustrated in the devices of FIGS. 4 and 14-15 Such sample ring has the advantage of total containment because its ends are welded to itself. The result is a closed system in one step without compromising the sample, system or operator The sample can be either a plain section of tube or can include a process module such as a filter or separator as part of its length.

Another feature of the invention is its ability to perform an injecting operation. In this respect, the invention is capable of inserting a sample or process module such as described with respect to FIG. 7-8 and 14-15. The module could be inserted into a closed system in one step again without compromising the sample, system or operator. This is particularly advantageous in biotechnology reactors which require absolute sterility yet require periodic nutrients supply and reagent injection and sample taking.

A further advantage of the invention is that ability to replace a tube section by removing a sample or process module and simultaneously inserting another tube section or process module in one step without compromising the first sample, new sample, system or operator. If desired, the original process module or tube section can be used as a sample ring. Such aspect is particularly useful for tracking of the system or perhaps so that the result of an assay on the sample ring could be attached to the used container to warn future users of possible biohazards. The user would be presented with a label similar to the labels on candy bars or cereal. A further advantage of the invention is the ability for replacing a process module. This could be accomplished by exchanging one supply (single port) container for another while simultaneously producing a safe sample ring for assay. This aspect would be useful in urinary drainage CAPD, blood processing, etc. The invention also permits the simultaneous exchange or "child" containers between two closed "parent" systems such as described with respect to FIG. 13-16. This aspect could be useful as a safe blood test For example, sample ring 80 would contain the blood to be tested. A pre-made reagent ring is then welded to the sample at the test center allowing the test reagent and blood to mix.

A further advantage of the invention is its ability to permit the addition of an assay device at the blood bank which could identify blood contaminated with the AIDS virus or hepatitis during the blood draw. A visual signal could warn operators of a potentially dangerous situation. The value of such aspect is that the blood presents a visual signal of contamination. Since the blood in effect labels itself there is no chance of mislabeling.

The invention is also capable of segmenting a system into two parts in one step without compromising the system or operator or requiring any additional equipment.

The invention thereby permits the safe handling of process fluids without the need for syringe needles, thereby minimizing the hazards of biological waste disposal As can be appreciated, the invention, thus has wide application in many fields. Some of these end uses include the following. For blood work the invention could be used for collection, processing, plasma pheresis or source plasma. Other end uses include CAPD, urinary drainage, chemotherapy, TPN (Total Parenteral Nutrition), hospital pharmacea, general use in biotech research and chemical laboratories, food and beverage processing, and pharmaceutical processing. In addition, the invention could be used in bio-tech, such as cell culturing, cell processing, or sampling - measuring.

What is claimed is

1. A process for introducing a process module into a main line wherein the process module is located in a plastic tube section closed at both ends and wherein the main line is a plastic tube including the steps of mounting the plastic tube section with each end located across a set of aligned grooves in a pair of side by side holders of two clamping assemblies, mounting the main tube across two sets of aligned grooves in the holders, clamping the tube section and main tube to the holders moving a wafer into a gap between the holders to cut through the tube section and main tube to thereby create eight cut ends, heating the cut ends to create melting, realigning the grooves so that the cut ends of the tube section on each side of the process module are aligned with corresponding cut ends of the main tube and with a portion of the main tube being separated from the remainder of the main tube, and pressing the realigned cut ends of the tube section which are realigned with the cut ends of the main tube to weld the realigned cut ends together and splice the process module into the main tube.

2. The process of claim 1 including providing a reagent in the process module

3. The process of claim 2 wherein the reagent is selected from the group consisting of nutrients, inoculants, pharmaceutics and color indicators 4. The process of claim 2 including providing a physical component in the process module and, said physical component being selected from the group consisting of filters, barriers, coatings, membranes and coagulants.

5. The process of claim 1 wherein the cut ends of the separated portion of the main tube are realigned with each other and welded together to form a ring sample simultaneously with the introduction of the process module into the main tube 6. The process of claim 5 wherein the ring sample contains a used process module.

7. A total containment process for closed systems using two plastic tubes including the steps of providing a pair of side by side clamping assemblies wherein each clamping assembly includes a holder having at least four tube receiving grooves extending thereacross, positioning the holders so that all of the grooves in one of the holders is aligned with corresponding grooves of the other holder, mounting the two plastic tubes across the holders in sets of aligned grooves, clamping the tubes to the holders, cutting through the tubes by a heated wafer to create a tube section in each groove and to also melt the cut ends of the tube sections, longitudinally moving one of the holders to realign its grooves with respect to the grooves of the other holder, disposing a tube section of one holder from one of the tubes in alignment with a tube section from the other of the tubes of the other holder, moving the aligned tube sections into contact with each other to weld the aligned tube sections into contact with each other to weld the aligned tube sections together, one of the tubes being a new tube which prior to the realignment step extends at one end across one set of aligned grooves and at the other end across a second set of aligned grooves and wherein the other of the tubes is a used tube which prior to the realignment step extends across a set of aligned grooves and across a further set of aligned grooves and wherein after the tube sections are cut and the holders are realigned two sets of tube sections of the holders are aligned with each other and four tube sections are located in grooves which are disposed out of alignment with any other grooves, sealing the four tube sections in the non-aligned grooves, and welding the aligned tube sections together.

8. A total containment process for closed systems using plastic tubes including the steps of providing a pair of side by side clamping assemblies wherein each clamping assembly includes a holder having at least two tube receiving grooves extending thereacross, positioning the holders so that all of the grooves in one of the holders is aligned with corresponding grooves of the other holder, mounting at least two plastic tube sections across the holders in sets of aligned grooves, clamping the tube sections to the holders, cutting through the tube sections by a heated water to also melt the cut ends of the tube sections, longitudinally moving one of the holders to realign its grooves with respect to the grooves of the other holder, disposing at least one tube section of one holder in alignment with a different tube section the tubes of the other holder, moving the tube sections into contact with each other to weld the aligned tube sections together, one of the tubes being closed at one end and has a new bag at the other end, another of the tubes leading to a patient at one end and having a used bag at the other end, before the sections are cut the tube having the new bag being disposed across one pair of aligned grooves and also across a second set of aligned grooves and the tube having the used bag being disposed across a single pair of aligned grooves, and after tube sections are cut and the grooves are realigned, a tube section communicating with the new bag being welded to a tube section leading to the patient and a tube section communicating with the used bag communicating with a tube section having a closed end and a third tue section being formed which is sealed at both ends.

9. A total containment process for closed systems using plastic tubes including the steps of providing a pair of side by side clamping assemblies wherein each clamping assembly includes a holder having at least two tube receiving grooves extending thereacross, positioning the holders so that all of the grooves in one of the holders is aligned with corresponding grooves of the other holder, mounting at least two plastic tube sections across the holders in sets of aligned grooves, clamping the tube sections to the holders, cutting through the tube sections by a heated water to also melt the cut ends of the tube sections, longitudinally moving one of the holders to realign its grooves with respect to the grooves of the other holder, disposing at least one tube section of one holder in alignment with a different tube section the tubes of the other holder, moving the tube sections into contact with each other to weld the aligned tube sections together, one of the tubes being disposed across the holders, one of said tubes being a main tube which extends across two set of aligned grooves and the other of the tube being a closed tube having a reagent therein, and after the tube sections are cut and realigned the portion of the tube having the reagent is welded to two sections of the main tube to crate flowed communication between two sections of the main tube and the tube section having the reagent.

10. A total containment process for closed systems using plastic tubes including the steps of providing a pair of side by side clamping assemblies wherein each clamping assembly includes a holder having at least two tube receiving grooves extending thereacross, positioning the holders so that all of the grooves in one of the holders is aligned with corresponding grooves of the other holder, mounting at least two plastic tube sections across the holders in sets of aligned grooves, clamping the tube sections to the holders, cutting through the tube sections by a heated water to also melt the cut ends of the tube sections, longitudinally moving one of the holders to realign its grooves with respect to the grooves of the other holder, disposing at least one tube section of one holder in alignment with a different tube section of the other holder, moving the tube sections into contact with each other to weld the aligned tube sections together, each holder having four sets of grooves, and simultaneously cutting and then simultaneously welding two sets of tubes having their tube sections in the four sets of grooves.

11. A total containment process for closed systems using plastic tubes including the steps of providing a pair of side by side clamping assemblies wherein each clamping assembly includes a holder having at least two tube receiving grooves extending thereacross, positioning the holders so that all of the grooves in one of the holders is aligned with corresponding grooves of the other holder, mounting at least two plastic tube sections across the holders in sets of aligned grooves, clamping the tube sections to the holders, cutting through the tube sections by a heated water to also melt the cut ends of the tube sections, longitudinally moving one of the holders to realign its grooves with respect to the grooves of the other holder, disposing at least one tube section of one holder in alignment with a different tube section of the other holder, moving the tube sections into contact with each other to weld the aligned tube sections together, mounting a single tube extending across two sets of aligned grooves in the holders before the heating and melting step with an intermediate portion of the tube extending from a groove in one holder to a non-aligned groove in the other holder and with the intermediate portion of the tube having two free ends in grooves aligned with each other after the realignment step, and welding the free ends together to form a ring sample.

12. The process of claim 11 wherein one of the tube sections contains a process module, and utilizing the weld step to introduce the process module into the other of the tube sections.

13. The process of claim 12 including providing a physical component in the process module, and the physical component being selected from the group consisting of filters, barriers, coating, membranes and coagulants.

14. The process of claim 12 including forming the ring sample simultaneously with the introduction of the process module.

15. The process of claim 12 including providing a reagent in the process module.

16. The process of claim 15 wherein the reagent is selected from the group consisting of nutrients, inoculants, pharmaceutics and color indicators.

17. The process of claim 11 wherein the ring sample contains a used process module.

* * * * *